US012605054B2

(12) United States Patent
Sasaguchi et al.

(10) Patent No.: US 12,605,054 B2
(45) Date of Patent: Apr. 21, 2026

(54) ENDOSCOPE AND ENDOSCOPE SYSTEM

(71) Applicant: OLYMPUS CORPORATION, Tokyo (JP)

(72) Inventors: Kazuya Sasaguchi, Hachioji (JP); Soichi Ikuma, Akishima (JP); Eijiro Sato, Hachioji (JP); Hiroki Kazuno, Kodaira (JP)

(73) Assignee: Olympus Corporation, Tokyo (JP)

( * ) Notice: Subject to any disclaimer, the term of this patent is extended or adjusted under 35 U.S.C. 154(b) by 316 days.

(21) Appl. No.: 18/239,296

(22) Filed: Aug. 29, 2023

(65) Prior Publication Data

US 2023/0404378 A1    Dec. 21, 2023

Related U.S. Application Data

(63) Continuation of application No. PCT/JP2021/041407, filed on Nov. 10, 2021.

(Continued)

(51) Int. Cl.
*A61B 1/00* (2006.01)
*A61B 1/015* (2006.01)
(Continued)

(52) U.S. Cl.
CPC .......... *A61B 1/015* (2013.01); *A61B 17/2202* (2013.01); *A61B 18/26* (2013.01);
(Continued)

(58) Field of Classification Search
CPC ..... A61B 1/015; A61B 1/00–32; A61B 1/018; A61B 1/307; A61B 1/00071;
(Continued)

(56) References Cited

U.S. PATENT DOCUMENTS

2005/0209507 A1* 9/2005 Suzuki ..................... A61L 2/26
600/101
2007/0038157 A1 2/2007 Yamada et al.
(Continued)

FOREIGN PATENT DOCUMENTS

CN          104720733 A      6/2015
CN          112153929 A      12/2020
(Continued)

OTHER PUBLICATIONS

International Search Report (with partial translation) and Written Opinion dated Jan. 25, 2022, issued in corresponding International Patent Application No. PCT/JP2021/041407.

(Continued)

*Primary Examiner* — Anh Tuan T Nguyen
*Assistant Examiner* — James Edward Boice
(74) *Attorney, Agent, or Firm* — Morgan, Lewis & Bockius LLP

(57) ABSTRACT

An endoscope includes an insertion portion that is inserted into a subject, and a suction channel that suctions a liquid along with a crushed calculus. The suction channel includes a channel main body, which is inserted in the insertion portion, and a small-diameter channel portion that is provided on a distal end side of the channel main body and has an inner diameter smaller than an inner diameter of the channel main body. The suction channel is configured to satisfy the relational expression R1/R2>1.27, where R1 represents the inner diameter of the channel main body and R2 represents the inner diameter of the small-diameter channel portion.

10 Claims, 8 Drawing Sheets

Related U.S. Application Data

(60) Provisional application No. 63/155,337, filed on Mar. 2, 2021.

(51) Int. Cl.
  *A61B 17/22* (2006.01)
  *A61B 18/26* (2006.01)

(52) U.S. Cl.
  CPC ............... *A61B 2017/22079* (2013.01); *A61B 2218/007* (2013.01)

(58) Field of Classification Search
  CPC ............ A61B 1/00087; A61B 1/00094; A61B 17/2202; A61B 18/26; A61B 18/24; A61B 2017/22079; A61B 2017/22074; A61B 2017/3445; A61B 2017/22072; A61B 2218/007; A61B 2218/00511; A61B 2218/00982
  USPC ........... 600/108, 387, 156; 606/2.5; 604/264

See application file for complete search history.

(56) References Cited

U.S. PATENT DOCUMENTS

| | | | |
|---|---|---|---|
| 2010/0210908 A1* | 8/2010 | Ashida ................ | A61B 1/0016 600/145 |
| 2013/0060169 A1 | 3/2013 | Yamada et al. | |
| 2016/0166320 A1 | 6/2016 | Ciulla et al. | |
| 2021/0085158 A1 | 3/2021 | Ikuma et al. | |

FOREIGN PATENT DOCUMENTS

| | | | | |
|---|---|---|---|---|
| EP | 1813218 A1 | 8/2007 | | |
| JP | 2000-175866 A | 6/2000 | | |
| JP | 2013-106770 A | 6/2013 | | |
| JP | 2018-500986 A | 1/2018 | | |
| JP | WO 2018/168070 A1 * | 9/2018 | ............... | A61B 1/00 |
| WO | 2006/048966 A1 | 5/2006 | | |
| WO | 2012/063825 A1 | 5/2012 | | |
| WO | 2018/168070 A1 | 9/2018 | | |
| WO | 2021/024487 A1 | 2/2021 | | |

OTHER PUBLICATIONS

Office Action dated Jan. 30, 2026, issued in corresponding Chinese Patent Application No. 202180094923.6.

* cited by examiner

ENDOSCOPE AND ENDOSCOPE SYSTEM

CROSS REFERENCE TO RELATED APPLICATION

This application is a continuation application of PCT/JP2021/041407 filed on Nov. 10, 2021 and claims benefit of U.S. Provisional Patent Application No. 63/155,337 filed in the U.S.A. on Mar. 2, 2021, the entire contents of which are incorporated herein by this reference.

BACKGROUND OF THE INVENTION

1. Field of the Invention

The present invention relates to an endoscope and an endoscope system configured to suction a liquid along with crushed calculus via a suction channel.

2. Description of the Related Art

In recent years, there have been proposed various technologies for crushing a calculus into small fragments and collecting the fragments, when removing the calculus from an organ such as a kidney of a subject.

One of the methods which are used for crushing the calculus is a method of generating laser light from a laser device. This is a method of inserting a ureteroscope into the organ of the subject, inserting a laser probe which is connected to the laser device into a treatment instrument channel of the ureteroscope, irradiating the calculus with laser light emitted from the laser probe, and thereby crushing the calculus.

For example, Japanese Patent Application Laid-Open Publication No. 2018-500986 describes that in a medical device including an image pickup device and an illumination device disposed on a distal end face of a tube, a suction port having an opening portion on the distal end face of the tube, and a plurality of water feeding ports arranged on a side face of the tube, a laser probe for crushing the calculus is inserted into the suction port. Here, an inner diameter of the suction port is constant from the distal end to the proximal end, the outer diameter of the laser probe is configured to be smaller than the inner diameter of the suction port, and a gap is formed between the suction port and the laser probe. The calculus crushed by irradiation with the laser light emitted from the laser probe is collected from the gap between the suction port and the laser probe, along with a liquid supplied from the water feeding port.

SUMMARY OF THE INVENTION

An endoscope according to one aspect of the present invention includes: an insertion portion configured to be inserted into a subject; and a suction channel that includes a channel main body inserted in the insertion portion, and a small-diameter channel portion which is provided on a distal end side of the channel main body, includes a channel opening in a distal end face of the insertion portion, and has an inner diameter smaller than an inner diameter of the channel main body, the suction channel being configured to suction, from the channel opening, a liquid along with a crushed calculus, wherein the suction channel is configured to satisfy the following relational expression:

$$R1/R2 > 1.27,$$

where R1 represents an inner diameter of the channel main body and R2 represents an inner diameter of the small-diameter channel portion.

An endoscope system according to one aspect of the present invention includes: an endoscope that includes an insertion portion configured to be inserted into a subject, and a suction channel that includes a channel main body inserted in the insertion portion, and a small-diameter channel portion which is provided on a distal end side of the channel main body, includes a channel opening in a distal end face of the insertion portion, and has an inner diameter smaller than an inner diameter of the channel main body, the suction channel being configured to suction, from the channel opening, a liquid along with a crushed calculus; and a calculus crushing device that includes a probe configured to protrude from the insertion portion and crush the calculus, and a generator configured to supply energy to the probe, wherein the suction channel is configured to satisfy the following relational expression:

$$R1/R2 > 1.27,$$

where R1 represents an inner diameter of the channel main body and R2 represents an inner diameter of the small-diameter channel portion.

DETAILED DESCRIPTION OF THE PREFERRED EMBODIMENTS

Figure 1:
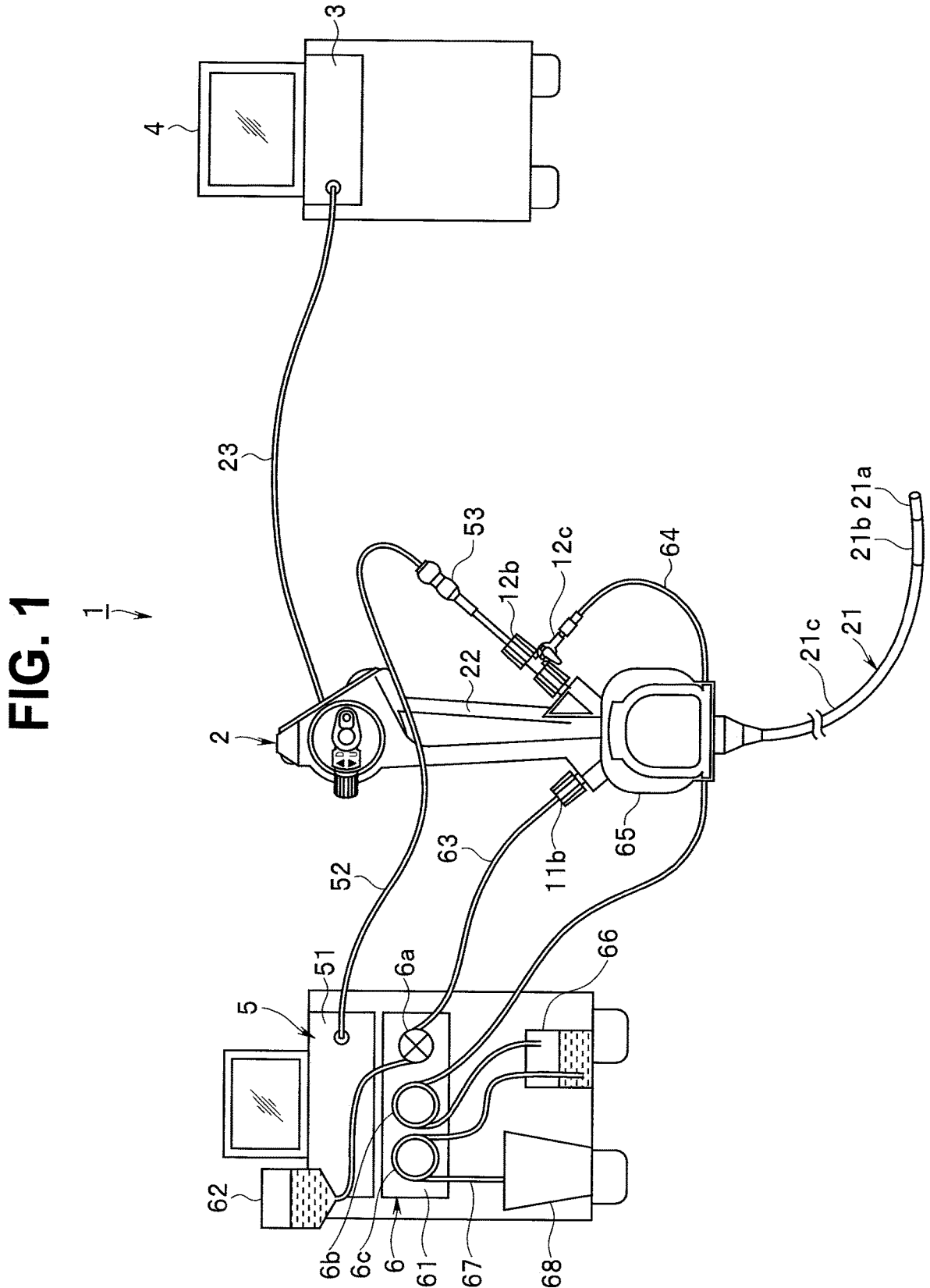
FIG. 1 is a view showing one configuration example of an endoscope system according to a first embodiment of the present invention.

Embodiments of the present invention will be described below with reference to the drawings. However, the present invention is not limited to the embodiments to be described below.

Note that in the description of the drawings, the same or corresponding elements are appropriately denoted by the same reference numerals. In addition, it should be noted that the drawings are schematic, and a relationship between lengths of elements, a ratio between lengths of elements, a quantity of elements, and the like in one drawing are different from reality in order to simplify the description, in some cases. Furthermore, even in relations among a plurality of drawings, there are cases where portions are included in which the mutual relationships and ratios between lengths are different.

First Embodiment

FIG. 1 to FIG. 9 show a first embodiment of the present invention, and FIG. 1 is a view showing one configuration example of an endoscope system 1.

As shown in FIG. 1, the endoscope system 1 of the present embodiment includes an endoscope 2, an endoscope control device 3, a monitor 4, a laser system 5 (calculus crushing device), and a pump system 6 (liquid feeding/suctioning device).

The endoscope 2 is a device with which a subject is observed and treated. The endoscope 2 includes: an elongated insertion portion 21 which is inserted into the subject; an operation portion 22 which is consecutively installed in a proximal end side of the insertion portion 21; and a universal cable 23 which extends from the operation portion 22. Note that the subject in which the insertion portion 21 is inserted is assumed to be a living organism such as a human being or an animal, but is not limited thereto, and may be a non-living organism such as a machine or a building.

Figure 2:
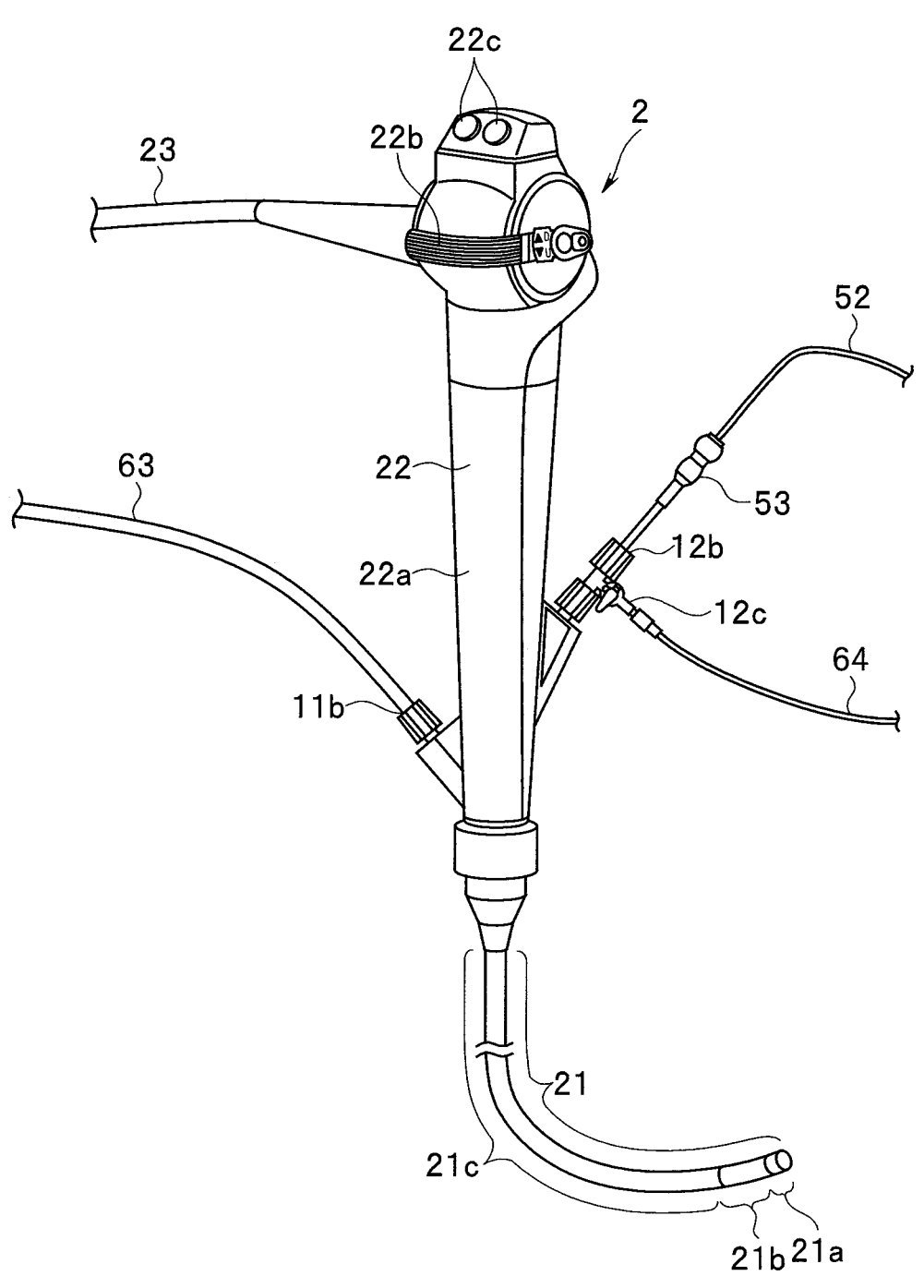
FIG. 2 is a view showing one configuration example of an endoscope according to the above first embodiment.

FIG. 2 is a view showing a configuration example of the endoscope 2.

As shown in FIG. 2, the insertion portion 21 includes a distal end portion 21*a*, a bending portion 21*b*, and a tubular portion 21*c* in order from the distal end toward the proximal end.

The distal end portion 21*a* includes an observation system and an illumination system. The observation system includes an observation window 13 (see FIG. 6 and the like) and an objective optical system; and further includes an image pickup device when the endoscope 2 is an electronic endoscope, and an image guide when the endoscope 2 is an optical endoscope. In the following description, it is assumed that the endoscope 2 is an electronic endoscope. The image pickup device includes an image sensor such as a CMOS or a CCD, and is connected to a signal wire. Note that the observation window 13 may also serve as a distal end lens of the objective optical system.

The illumination system includes, for example, an illumination window 14 (see FIG. 6 and the like) which also serves as an illumination optical system, and a light guide.

The light guide is configured, for example, as a fiber bundle in which optical fibers are bundled. A signal wire which is connected to the image pickup device and the light guide are disposed in the insertion portion 21, the operation portion 22, and the universal cable 23, and are connected to the endoscope control device 3.

Figure 3:
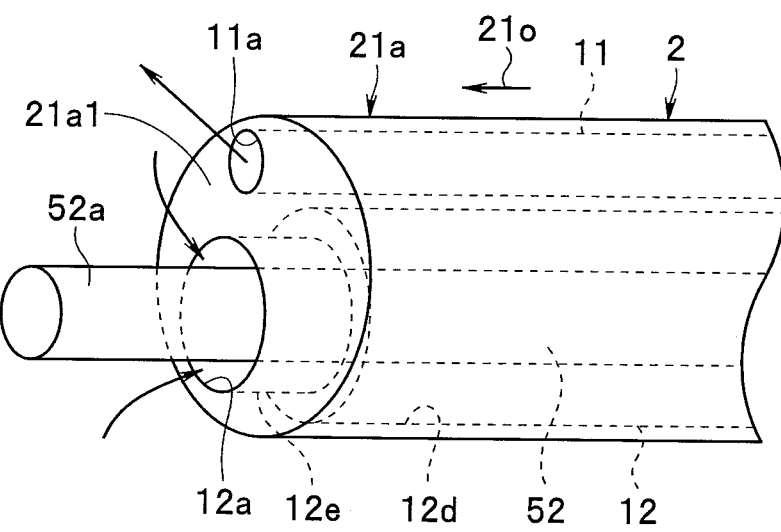
FIG. 3 is a perspective view showing a state of a distal end portion of the endoscope into which a laser probe is inserted, in the above first embodiment.
Figure 4:
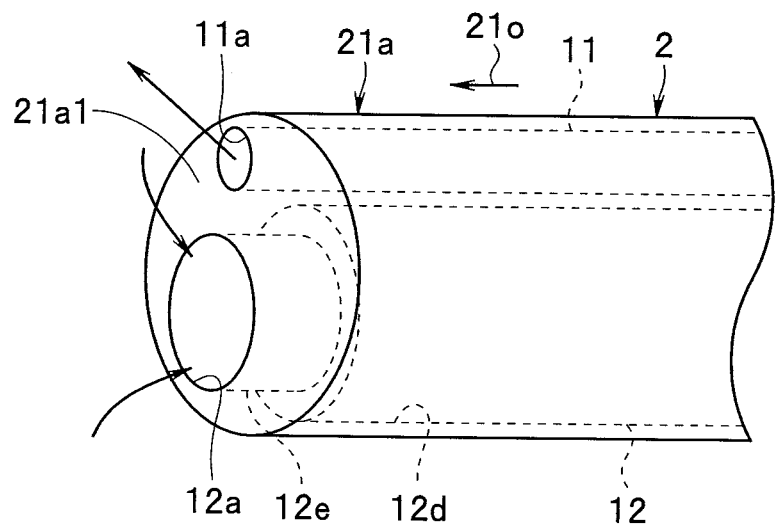
FIG. 4 is a view showing a state of the distal end portion of the insertion portion of the endoscope after the laser probe has been removed, in the above first embodiment.

FIG. 3 is a perspective view showing a state of the distal end portion 21*a* of the endoscope 2 in which a laser probe 52 is inserted. FIG. 4 is a view showing a state of the distal end portion 21*a* of the insertion portion 21 of the endoscope 2 after the laser probe 52 has been removed.

As shown in FIG. 3 and FIG. 4, a liquid feeding channel 11 which conveys a liquid therethrough and a suction channel 12 which also serves as a treatment instrument channel are inserted in the insertion portion 21. The liquid feeding channel 11 has, for example, a constant inner diameter, and is provided with a channel opening 11*a* on the distal end face 21*a*1 of the distal end portion 21*a*. The suction channel 12 includes a channel main body 12*d* which is inserted in the insertion portion 21, and a small-diameter channel portion 12*e* which is provided on the distal end side of the channel main body 12*d*.

The small-diameter channel portion 12*e* has a channel opening 12*a* (treatment instrument opening) in the distal end face 21*a*1 of the distal end portion 21*a*. In any of states at the time when the laser probe 52 is inserted in the suction channel 12 as shown in FIG. 3 and after the laser probe 52 has been removed from the suction channel 12 as shown in FIG. 4, the suction channel 12 suctions the liquid along with the crushed calculus from the channel opening 12*a*.

The bending portion 21*b* is consecutively installed in a proximal end side of the distal end portion 21*a*, and is configured to be bendable in two directions, or four directions of up, down, left and right directions, for example. When the bending portion 21*b* is bent, the direction of the distal end portion 21*a* changes, and the direction of observation by the observation system and the irradiation direction of the illumination light by the illumination system change. In addition, the bending portion 21*b* is also bent in order to enhance the insertability of the insertion portion 21 in the subject.

The tubular portion 21*c* is a tubular region that connects the proximal end of the bending portion 21*b* with the distal end of the operation portion 22. The tubular portion 21*c* may be in a rigid form in which the insertion portion 21 does not bend, or may be in a flexible form in which the insertion portion 21 bends according to the shape of the subject in which the insertion portion 21 is inserted. An endoscope having a rigid insertion portion is generally referred to as a rigid endoscope, and an endoscope having a flexible insertion portion is generally referred to as a flexible endoscope. For example, rigid endoscopes and flexible endoscopes in a medical field are defined in ISO8600-1: 2015.

The operation portion 22 is a region that is consecutively installed in the proximal end side of the insertion portion 21, and which an operator grasps by a hand to perform various operations related to the endoscope 2. The operation portion 22 includes: for example, a grasping portion 22*a*; a bending operation lever 22*b*; a plurality of operation buttons 22*c*; a channel opening 11*b* on the proximal end side of the liquid feeding channel 11; a channel opening 12*b* on the proximal end side of the suction channel 12; and a suction tube connector 12*c* of the suction channel 12.

The grasping portion 22*a* is a region where the operator grasps the endoscope 2 with the palm.

The bending operation lever 22*b* is an operation device by which the operator performs an operation of bending the bending portion 21b while using, for example, a thumb or the like of the hand that grasps the grasping portion 22a.

The plurality of operation buttons 22c include, for example, a liquid feeding button and a suction button. The liquid feeding button is an operation button for feeding a liquid to the distal end portion 21a side via the liquid feeding channel 11. The suction button is an operation button for suction from the distal end portion 21a side via the suction channel 12. In addition, the plurality of operation buttons 22c may include, for example, a button switch for an operation related to image pickup (release operation or the like).

The channel opening 11b on the proximal end side of the liquid feeding channel 11 is provided on one side face on the distal end side of the grasping portion 22a. A liquid feeding tube 63 is connected to the channel opening 11b.

The channel opening 12b on the proximal end side of the suction channel 12 is provided on the other side face on the distal end side of the grasping portion 22a. The laser probe 52 is inserted into the channel opening 12b of the suction channel 12 which also serves as a treatment instrument channel, with the use of the protection tube 53. The protection tube 53 prevents breakage of the laser fiber which the laser probe 52 includes. Note that the suction channel 12 is used for inserting various treatment instruments therein. Accordingly, a treatment instrument such as forceps may be inserted into the suction channel 12, in place of the laser probe 52.

The suction channel 12 suctions the liquid in the subject along with the crushed calculus. A first suction tube 64 is connected to the suction tube connector 12c which is provided near the channel opening 12b, on the proximal end side of the suction channel 12.

The universal cable 23 extends from a side face of the proximal end side of the operation portion 22, and is connected to the endoscope control device 3.

The endoscope control device 3 also serves as an image processing device and a light source device; controls the endoscope 2; processes an image pickup signal which is acquired from the endoscope 2; and supplies illumination light to the endoscope 2.

The endoscope control device 3 includes: a plurality of light sources that emit illumination light such as white light or light for special observation; a light source control circuit that controls the light sources; and an optical system that collects light emitted from the light sources to an incident end of the light guide. Any light source such as an LED (light emitting diode) light source, a laser light source, a xenon light source or a halogen light source may be used as long as the light source is a device that emits illumination light, and a plurality of types of light sources may be combined.

Note that the image processing device and the light source device may be configured as separate devices. In addition, in place of the configuration in which the illumination light is supplied from the endoscope control device 3 to the endoscope 2, the configuration may be employed in which a light emitting device arranged in the distal end portion 21a emits the illumination light.

A portion which performs light source control, image processing, and various types of control in the endoscope control device 3 is configured to accomplish all or one part of the functions of the respective units by that a processor such as an ASIC (application specific integrated circuit) or an FPGA (field programmable gate array) including a CPU (central processing unit) or the like reads a computer program (software) which is stored, for example, in a nontransitory computer-readable storage device such as a ROM (read-only memory) (or an HDD (hard disk drive), an SSD (solid state drive), or a disk-shaped recording medium), expands the computer program in a RAM (random access memory), and executes the computer program. However, the present invention is not limited to the configuration, and the endoscope control device 3 may be configured to accomplish all or one part of the functions of the respective units, for example, by a dedicated electronic circuit.

Due to a connection of the universal cable 23 to a connector receiver of the endoscope control device 3, the endoscope 2 and the endoscope control device 3 are electrically and optically connected to each other.

The illumination light emitted from the endoscope control device 3 which also serves as the light source device is transmitted by the light guide, and the subject is irradiated with the illumination light through the illumination window 14 of the distal end portion 21a. Return light from the subject which has been irradiated with the illumination light passes through the observation window 13, and forms an image on the image pickup device due to the objective optical system.

The endoscope control device 3 transmits a drive signal and an electric power to the image pickup device. The image pickup device captures an optical image of the subject according to the drive signal, and generates an image pickup signal. Image pickup by the image pickup device is sequentially performed on a frame-by-frame basis, for example, and image pickup signals related to a moving image of a plurality of frames are generated. The image pickup signal is transmitted to the endoscope control device 3 via the signal wire.

The endoscope control device 3 receives the image pickup signal obtained by the image pickup device, performs various types of image processing such as demosaicking, noise correction, color correction, contrast correction and gamma correction, and generates a displayable image signal. The endoscope control device 3 may superimpose various types of information such as character information and guide information, on the image signal.

The image signal generated by the endoscope control device 3 is outputted to the monitor 4. The monitor 4 is a display device that receives the image signal from the endoscope control device 3, and displays an endoscope image thereon.

The laser system 5 is a calculus crushing device that includes a laser apparatus main body 51 and a laser probe 52. The laser apparatus main body 51 is a generator that generates laser light (energy) for crushing calculus (urolithiasis) in urinary tracts in a kidney, the ureter, the bladder, the urethras and the like, and supplies the laser light to the laser probe 52. The laser probe 52 includes a laser fiber that transmits the laser light. The probe distal end 52a of the laser probe 52 is extended from the channel opening 12a on the distal end side of the suction channel 12, and the laser light is generated by the laser apparatus main body 51. Then, the calculus in the subject is irradiated with the laser light, transmitted by the laser probe 52, from the probe distal end 52a, and the calculus is crushed.

Note that the laser system 5 has been described as an example of the calculus crushing device in the present embodiment, but the present invention is not limited thereto, and any device capable of crushing the calculus may be used. For example, when the calculus is crushed with the use of ultrasound, an ultrasound probe and an ultrasound device which is a generator for supplying energy to the ultrasound probe may be used as a calculus crushing device, in place of the laser probe 52 and the laser apparatus main body 51.

The pump system 6 includes: a pump main body 61, which has a liquid feeding pump 6*a*, a first suction pump 6*b* and a second suction pump 6*c*; a liquid feeding tank 62; a liquid feeding tube 63; a first suction tube 64; a first filter 65; a second filter 66; a second suction tube 67; and a waste tank 68.

The liquid feeding tank 62 stores a liquid which is to be fed into the subject. A liquid which is stored in the liquid feeding tank 62 is, for example, a physiological saline.

The liquid feeding tank 62 is connected to the liquid feeding pump 6*a* by a liquid feeding tube 63, and the liquid feeding tube 63 on the distal end side of the liquid feeding pump 6*a* is connected to the channel opening 11*b* on the proximal end side of the liquid feeding channel 11.

When the liquid feeding pump 6*a* is operated, the liquid in the liquid feeding tank 62 is fed through the liquid feeding tube 63, passes through the liquid feeding channel 11, and is discharged into the subject from the channel opening 11*a* on the distal end side.

When the first suction tube 64 is connected to the suction tube connector 12*c*, the first suction tube 64 communicates with an inner part of the suction channel 12. Even in the case where the laser probe 52 is inserted in the suction channel 12, suction by the first suction tube 64 is possible, because there is a gap between the laser probe 52 and the suction channel 12.

The first suction tube 64 is connected to the second filter 66 via the first filter 65 and the first suction pump 6*b*. The first filter 65 and the second filter 66 are instruments that filter the calculus or mucosa suctioned from the inside of the subject. Among the filters, for example, the first filter 65 is used for collecting the calculus. The first filter 65 is attached to, for example (but not limited to the arrangement), the distal end side of the grasping portion 22*a* in the operation portion 22 of the endoscope 2.

One end of the second suction tube 67 is connected to the second filter 66, and the other end thereof is connected to the waste tank 68 via the second suction pump 6*c*.

The first suction pump 6*b* and the second suction pump 6*c* operate in conjunction with each other, and when the laser probe 52 is inserted in the suction channel 12, suction the liquid along with the calculus in the subject, from between the small-diameter channel portion 12*e* and the distal-end-side shaped portion 52*c*, via the channel opening 12*a* of the suction channel 12. At this time, the liquid feeding pump 6*a* also operates simultaneously, and thereby, a liquid is fed into the subject via the liquid feeding channel 11, and at the same time, the liquid in the subject is suctioned via the suction channel 12. The liquid discharged from the liquid feeding channel 11 is caused to generate a circulating flow in the subject, and the crushed calculus is caused to be carried by the flow; and thereby, the collection efficiency of the calculus by the pump system 6 is enhanced.

Figure 5:
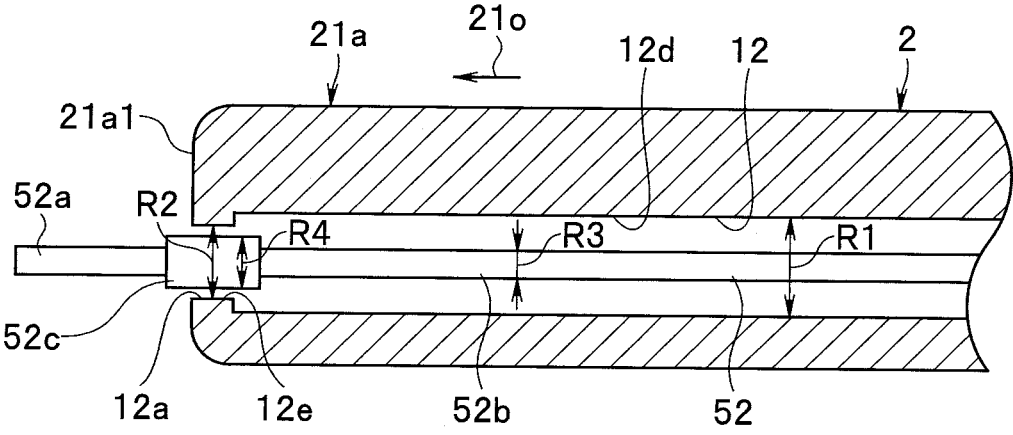
FIG. 5 is a cross-sectional view showing a configuration of a suction channel and a laser probe in the above first embodiment.
Figure 6:
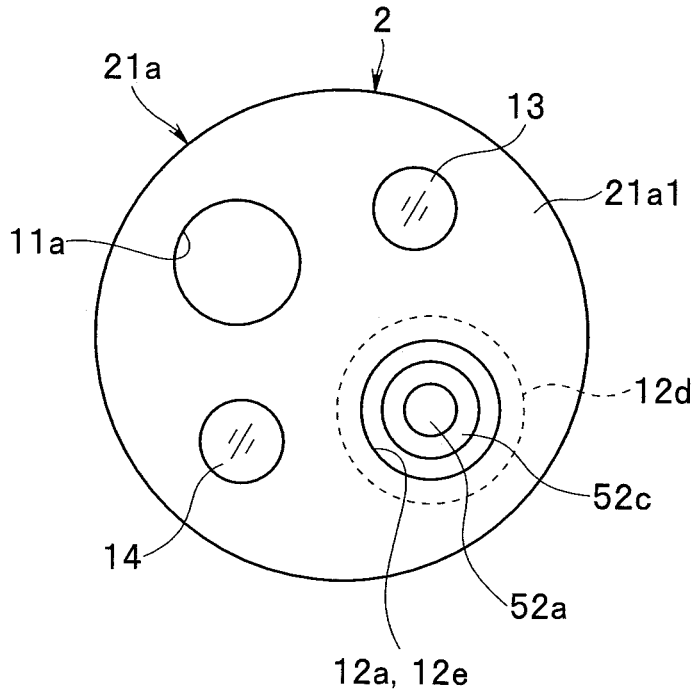
FIG. 6 is a front view showing a configuration of the distal end portion of the insertion portion of the endoscope according to the above first embodiment.

FIG. 5 is a cross-sectional view showing a structure of the suction channel 12 and the laser probe 52. FIG. 6 is a front view showing a configuration of the distal end portion 21*a* of the insertion portion 21 of the endoscope 2.

The channel main body 12*d* has a constant inner diameter R1 (see FIG. 5), for example, from the channel opening 12*b* on the proximal end side toward the distal end side. The small-diameter channel portion 12*e* which is provided on the distal end side of the channel main body 12*d* has an inner diameter R2 smaller than the inner diameter R1 of the channel main body 12*d* (R2<R1).

In a state in which the laser probe 52 is not inserted in the suction channel 12 as shown in FIG. 4, it varies depending on the magnitude of the inner diameter ratio R1/R2 (>1) between the inner diameter R1 of the channel main body 12*d* to the inner diameter R2 of the small-diameter channel portion, whether the calculus CS suctioned from the channel opening 12*a* along with the liquid clogs in the channel main body 12*d*, or is conveyed without clogging there.

Even though the small-diameter channel portion 12*e* has the inner diameter R2 smaller than the inner diameter R1 of the channel main body 12*d*, the clogging occurs when the inner diameter ratio R1/R2 is small because the calculus CS to be suctioned contains calculi having elongated shapes, in some cases.

Figure 7:
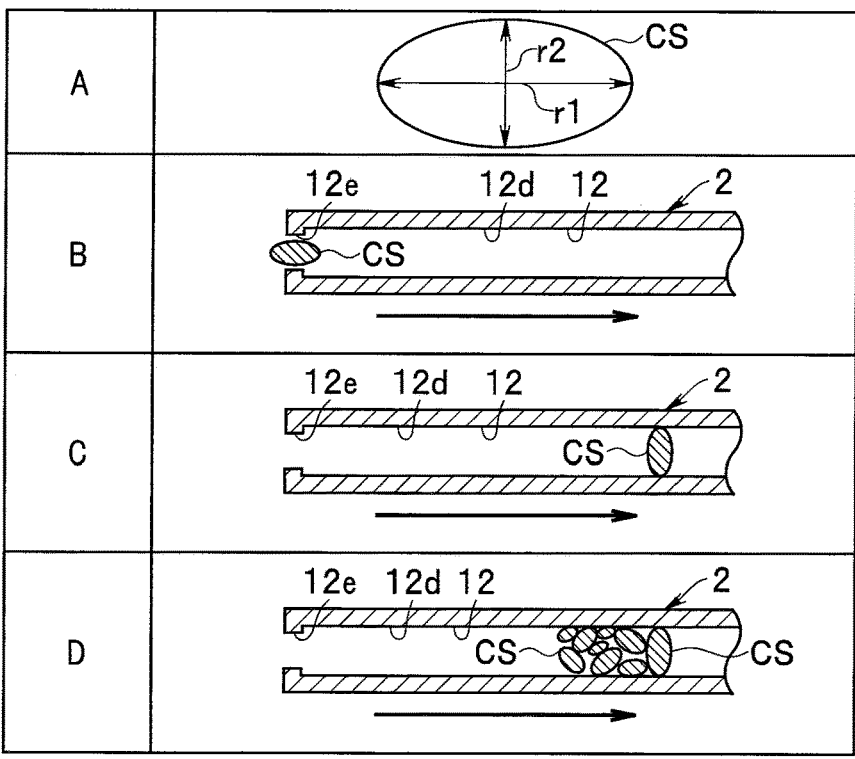
FIG. 7 is a diagram for describing an example in which a calculus suctioned via a small-diameter channel portion clogs in a channel main body, when the laser probe is not inserted in the suction channel, in the above first embodiment.

FIG. 7 is a diagram for describing an example in which the calculus CS suctioned via the small-diameter channel portion 12*e* clogs in the channel main body 12*d*, when the laser probe 52 is not inserted in the suction channel 12.

As shown in column A of FIG. 7, the length of the longest shaft in the crushed calculus CS shall be represented by r1, and the length of the longest diameter among the diameters perpendicular to the longest shaft shall be represented by r2. As one example, when the calculus CS is an ellipsoid in which lengths of three orthogonal diameters are a, b and c (a<b<c), r1=c and r2=b are satisfied.

As shown in column B of FIG. 7, if r2<R2 is satisfied, the calculus CS can pass through the small-diameter channel portion 12*e*, and be suctioned into the inner part of the channel main body 12*d*.

However, when the calculus CS further satisfies r1>R1, as shown in column C of FIG. 7, it occurs in some cases that the calculus CS is caught on an inner wall of the channel main body 12*d* in the inner part of the channel main body 12*d* and cannot move in the channel main body 12*d*.

Then, as shown in column D of FIG. 7, there is a possibility that the subsequent calculus CS stacks on the calculus CS caught on the inner wall of the channel main body 12*d*, and that clogging thereby occurs in the suction channel 12.

Figure 8:
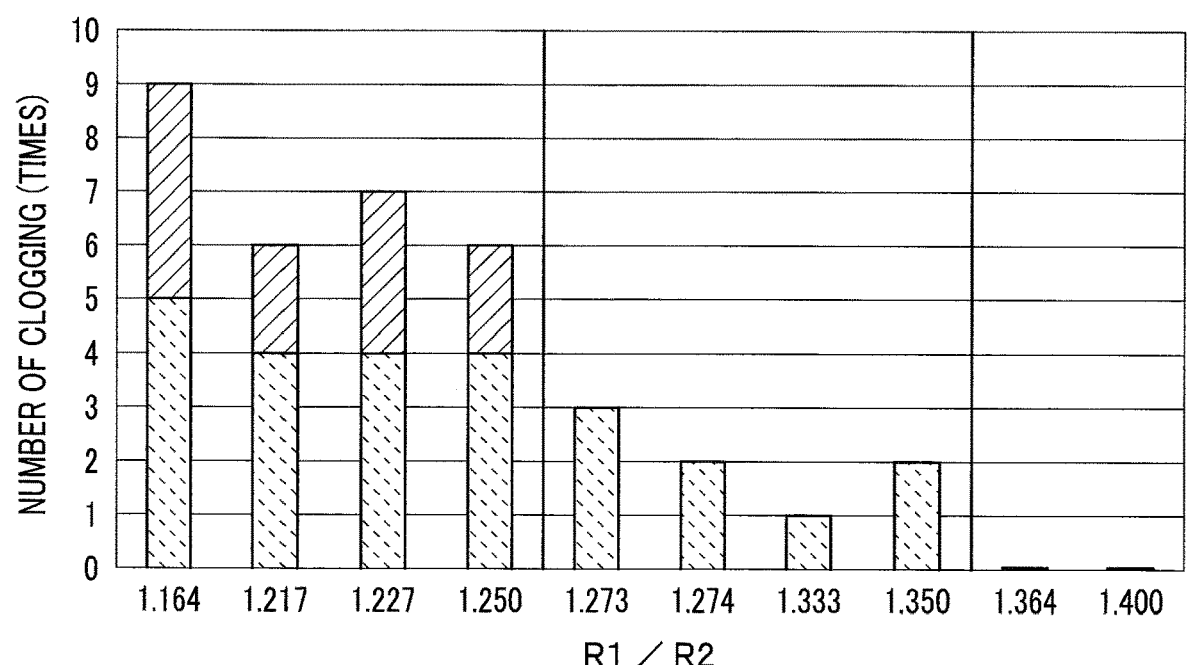
FIG. 8 is a bar graph describing an example in which a frequency of clogging of the calculus varies depending on a ratio of the inner diameters of the channel main body and the small-diameter channel portion, when the laser probe is not inserted in the suction channel, in the above first embodiment.

FIG. 8 is a bar graph for describing an example in which the frequency of the occurrence of clogging of the calculus varies depending on a ratio between the inner diameters of the channel main body 12*d* and the small-diameter channel portion 12*e*, when the laser probe 52 is not inserted in the suction channel 12. FIG. 8 shows a result of an experiment in which the number of times of occurrence of clogging has been measured, while the inner diameter ratio R1/R2 of the inner diameter R1 of the channel main body 12*d* to the inner diameter R2 of the small-diameter channel portion has been varied.

Note that in FIG. 8, a portion indicated by dotted line hatching indicates the number of times of occurrence of clogging that can be eliminated by backflow, and a portion indicated by solid line hatching indicates the number of times of occurrence of clogging that cannot be eliminated by the backflow.

Firstly, in the case of R1/R2>1.36 (range 1), the number of clogging is 0. Accordingly, the suctioned calculus CS is conveyed substantially without causing clogging in the channel main body 12*d*.

Next, in the case of 1.27<R1/R2<1.36 (range 2), the clogging rarely occurs. However, the clogging which has occurred can be eliminated by some method of causing the crushed calculus CS to flow backward to the distal end side.

One example of the method of causing the calculus CS to flow backward to the distal end side is a method of switching the connection between the liquid feeding channel 11 and the suction channel 12 in the middle, and feeding the liquid to the suction channel 12. Accordingly, the pump connected to the suction channel 12 is not limited to the suction pumps 6*b* and 6*c*, but can be the liquid feeding pump 6*a* in some cases. In addition, another example of the method of causing the backflow is a method of providing an electromagnetic valve in the middle of the suction channel 12, and opening the electromagnetic valve only for a short time period to open the inside of the suction channel 12 to the atmospheric pressure. Not limited to the methods, it is also acceptable to cause the calculus CS to flow backward with the use of an appropriate method.

In addition, in the case of 1<R1/R2<1.27 (range 3), the clogging occurs at a higher frequency than in the case of (range 2). In the clogging that occurs in the case of (range 3), not only clogging that can be eliminated by backflow but also clogging that cannot be eliminated by backflow is included in some cases. When clogging has occurred which cannot be eliminated by the backflow, it becomes necessary to take measures such as stopping the suction and feeding a pressurized liquid into the suction channel 12 with the use of a syringe or the like.

In the experimental results shown in FIG. 8, in the case of R1/R2>1.36 (range 1), the calculus CS is conveyed in the channel main body 12*d* without causing clogging. This is because when the calculus is crushed by the laser, there is an extremely low probability that the crushed calculus CS forms a shape that simultaneously satisfies r2<R2 and r1>R1. In other words, 1.36 which is a lower limit value of the inner diameter ratio at which the clogging of the calculus CS does not almost occur is a value that is experimentally determined according to the shape of the calculus CS crushed by the laser.

In addition, the laser probe 52 includes: a treatment instrument main body 52*b*, which has an outer diameter R3 (R3<R2), and a distal-end-side shaped portion 52*c* which has an outer diameter R4 (R4<R2). The laser probe 52 of the present embodiment is structured so that the distal-end-side shaped portion 52*c* has a larger diameter than the treatment instrument main body 52*b*, and so as to satisfy R4>R3. Note that in the illustrated example, the probe distal end 52*a* positioned in the distal end side with respect to the distal-end-side shaped portion 52*c* has, for example (but not limited to the structure), a same outer diameter R3 as the treatment instrument main body 52*b*.

In a state in which the laser probe 52 irradiates the calculus in the subject with the laser light from the probe distal end 52*a*, the treatment instrument main body 52*b* is inserted in the channel main body 12*d*, and the distal-end-side shaped portion 52*c* is inserted into the small-diameter channel portion 12*e*. In other words, when the laser probe 52 is extended by a length suitable for laser light irradiation from the distal end face 21*a*1 of the distal end portion 21*a*, the distal-end-side shaped portion 52*c* is disposed at a position corresponding to the small-diameter channel portion 12*e*.

At this time, the suction channel 12 and the laser probe 52 are configured to satisfy the following relational expression: R1–R3≥2(R2–R4) . . . (1).

(R1–R3)/2 represents a minimum value of widest gaps in the gaps between the treatment instrument main body 52*b* and the channel main body 12*d*, which are formed around the treatment instrument main body 52*b*. For example, when the outer surface of the treatment instrument main body 52*b* comes in contact with the inner surface of the channel main body 12*d*, there are formed a narrowest gap 0 in the contact portion and a widest gap (R1–R3) on the opposite side of the contact portion in the circumferential direction. In general, when the narrowest gap is represented by R0 (0≤R0≤{(R1–R3)/2}), the widest gap becomes {(R1–R3)–R0}. In addition, when the narrowest gap becomes R0=(R1–R3)/2, the widest gap and the narrowest gap are the same, and both become (R1–R3)/2. Thus, (R1–R3)/2 is the minimum value of the widest gaps.

In addition, (R2–R4) indicates a maximum diameter (the maximum diameter at the time when the calculus is assumed to have a spherical shape) of the calculus that can pass between the small-diameter channel portion 12*e* and the distal-end-side shaped portion 52*c*. Accordingly, the expression (1) indicates that even though a calculus having a maximum diameter that can pass through the channel opening 12*a* has entered the suction channel 12, there is a flow path having a distance of the maximum diameter or larger, in the gap between the treatment instrument main body 52*b* and the channel main body 12*d*, and the calculus can be suctioned without causing clogging.

Figure 9:
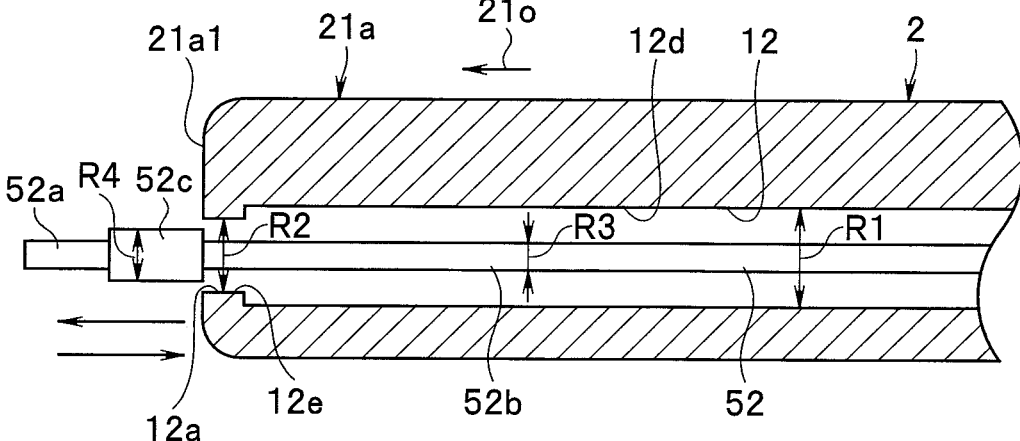
FIG. 9 is a view for describing an action for eliminating the clogging of the calculus between the small-diameter channel portion and a distal-end-side shaped portion, at the time when the laser probe is inserted in the suction channel, in the above first embodiment.

FIG. 9 is a view for describing an action of eliminating the clogging of the calculus between the small-diameter channel portion 12*e* and the distal-end-side shaped portion 52*c*, at the time when the laser probe 52 is inserted in the suction channel 12.

A calculus having a diameter larger than (R2–R4)/2 clogs in the gap between the small-diameter channel portion 12*e* and the distal-end-side shaped portion 52*c*, or on the distal end side of the channel opening 12*a*, in some cases. In particular, a calculus having a diameter larger than (R2–R4) cannot pass through the gap between the small-diameter channel portion 12*e* and the distal-end-side shaped portion 52*c*, and becomes a cause of the clogging.

The laser probe 52 can move in the suction channel 12 in an axial direction 210 of the insertion portion 21. Then, when the clogging has occurred between the small-diameter channel portion 12*e* and the distal-end-side shaped portion 52*c*, the laser probe 52 is pushed and moved in the axial direction 210 from the position shown in FIG. 5 so that the treatment instrument main body 52*b* is inserted in the small-diameter channel portion 12*e*, as shown in FIG. 9. After that, such an action is conducted that the laser probe 52 is pulled back to the position shown in FIG. 5. Note that it is acceptable to perform a back-and-forth motion of pulling back and then pushing, in place of a back-and-forth motion of pushing and then pulling back.

The flow path between the small-diameter channel portion 12*e* and the distal-end-side shaped portion 52*c* is narrower than the flow path between the channel main body 12*d* and the treatment instrument main body 52*b*. Because of this, if the calculus which has been sandwiched between the small-diameter channel portion 12*e* and the distal-end-side shaped portion 52*c* moves to the flow path between the channel main body 12*d* and the treatment instrument main body 52*b*, when the laser probe 52 is moved back and forth, the calculus is suctioned without causing clogging after that.

In addition, the calculus which has existed on the more distal end side than the gap between the channel opening 12*a* and the distal-end-side shaped portion 52*c* is separated from the distal end face 21*a*1 of the endoscope 2, due to the forward movement of the distal-end-side shaped portion 52*c* of the laser probe 52, and circulates again in the subject.

When such a back-and-forth motion of the laser probe 52 in the axial direction 210 is performed once or a plurality of times, the clogging of the calculus can be thereby eliminated. In addition, it is acceptable to further crush a calculus having such a size as not to be capable of passing through the gap between the small-diameter channel portion 12e and the distal-end-side shaped portion 52c, by laser irradiation.

Note that it is acceptable for an operator to perform the back-and-forth motion for the laser probe 52 manually, but it is also acceptable to provide a separate slide mechanism and mechanically move the laser probe 52.

In addition, in the above description, the case has been described in which the treatment instrument is the laser probe 52, as an example, but a treatment instrument other than the laser probe 52 may also be configured to satisfy the above described expression (1). For example, in a case where the liquid feeding channel 11 is omitted and the liquid feeding tube 63 is inserted in the suction channel 12 to perform liquid feeding, the liquid feeding tube 63 serving as a treatment instrument for feeding a liquid may be configured to satisfy the expression (1).

According to such a first embodiment, the suction channel 12 is configured to have the channel main body 12d, and the small-diameter channel portion 12e having an inner diameter smaller than the inner diameter of the channel main body 12d, and the suction channel 12 and the treatment instrument (the laser probe 52 and the like) have been configured to satisfy the expression (1) in particular; and accordingly, the calculus suctioned from the channel opening 12a can be conveyed without causing clogging in the channel main body 12d. Thus, according to the endoscope 2 and the endoscope system 1 of the present embodiment, it is possible to reduce the clogging in the suction channel 12.

In addition, such a distal-end-side shaped portion 52c is provided to satisfy R4>R3 in the treatment instrument (the laser probe 52 or the like), and thereby, the clogging in the suction channel 12 can be more reliably reduced.

Even though the clogging of the calculus has occurred in the gap between the small-diameter channel portion 12e and the distal-end-side shaped portion 52c, or on the distal end side of the channel opening 12a, the clogging can be easily eliminated, due to the back-and-forth motion of the treatment instrument.

The suction tube connector 12c has been provided in the suction channel 12, and thereby, the suction tube 64 can be connected thereto simply and reliably.

The calculus is irradiated with the laser light emitted from the laser probe 52 which is inserted in the suction channel 12, and thereby, the calculus can be accurately crushed under observation by the endoscope 2.

In addition, the suction channel 12 also serves as the treatment instrument channel, and thereby the diameter of the insertion portion 21 can be reduced as compared with the case where the treatment instrument channel is provided separately from the suction channel 12.

Second Embodiment

Figure 10:
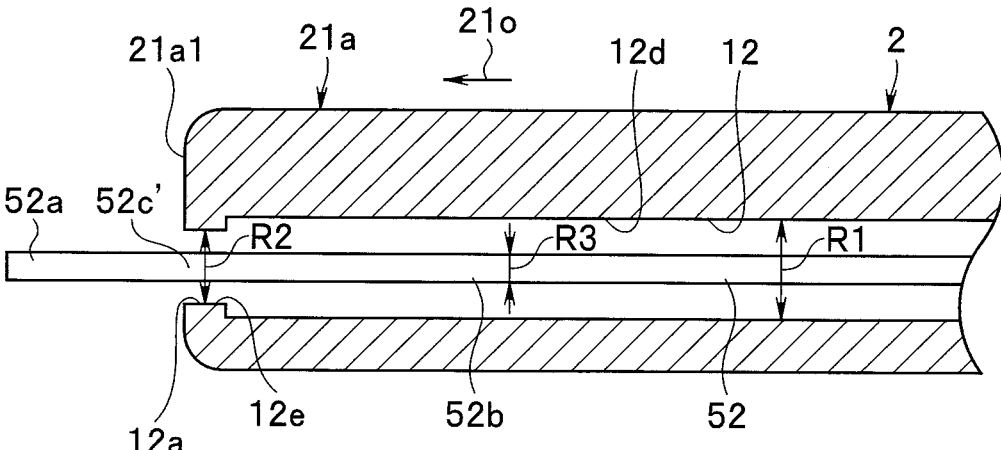
FIG. 10 is a cross-sectional view showing a structure of the suction channel and the laser probe in a second embodiment of the present invention.
Figure 11:
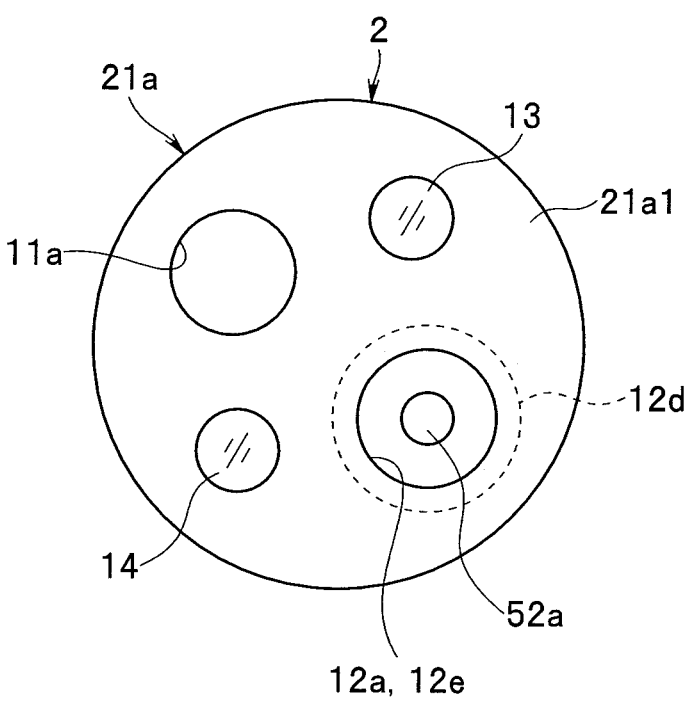
FIG. 11 is a front view showing a configuration of a distal end portion of an insertion portion of the endoscope, in the above second embodiment.

FIG. 10 and FIG. 11 show a second embodiment of the present invention, and FIG. 10 is a cross-sectional view showing a structure of the suction channel 12 and the laser probe 52. FIG. 11 is a front view showing a configuration of the distal end portion 21a of the insertion portion 21 of the endoscope 2. In the second embodiment, same portions as those in the first embodiment are denoted by same reference numerals, the description thereof will be appropriately omitted, and different points will be mainly described.

In the laser probe 52 of the present embodiment, the distal-end-side shaped portion 52c' which is inserted into the small-diameter channel portion 12e has a same outer diameter as an outer diameter of the treatment instrument main body 52b, and satisfies R4=R3; and the expression (1) is expressed as the following expression (2).

$$R1 - R3 \geq 2(R2 - R3) \tag{2}$$

The meaning of the expression (2) is the same as that described above in the expression (1), and a minimum value $(R1 - R3)/2$ of widest gaps that are formed between the channel main body 12d (inner diameter R1) and the laser probe 52 (outer diameter R3) becomes a maximum diameter $(R2 - R3)$ or larger of the calculus that can pass between the small-diameter channel portion 12e (inner diameter R2) and the laser probe 52.

Note that also in the present embodiment, a treatment instrument other than the laser probe 52 may be configured to satisfy the expression (2) in the same way.

According to such a second embodiment, substantially the same effects as those of the above described first embodiment are achieved, and the same effects as those of the first embodiment are obtained, even without a large diameter portion being provided on the distal end side of the treatment instrument (laser probe 52 or the like). Accordingly, a treatment instrument having a special shape is not required, and a general-purpose treatment instrument can be used.

Related Embodiment

Figure 12:
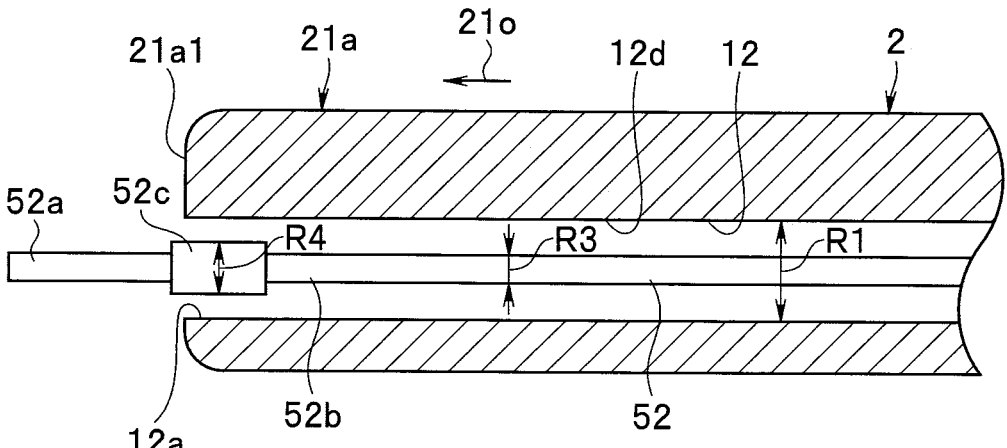
FIG. 12 is a cross-sectional view showing a structure of the suction channel and the laser probe, in a related embodiment of the present invention.
Figure 13:
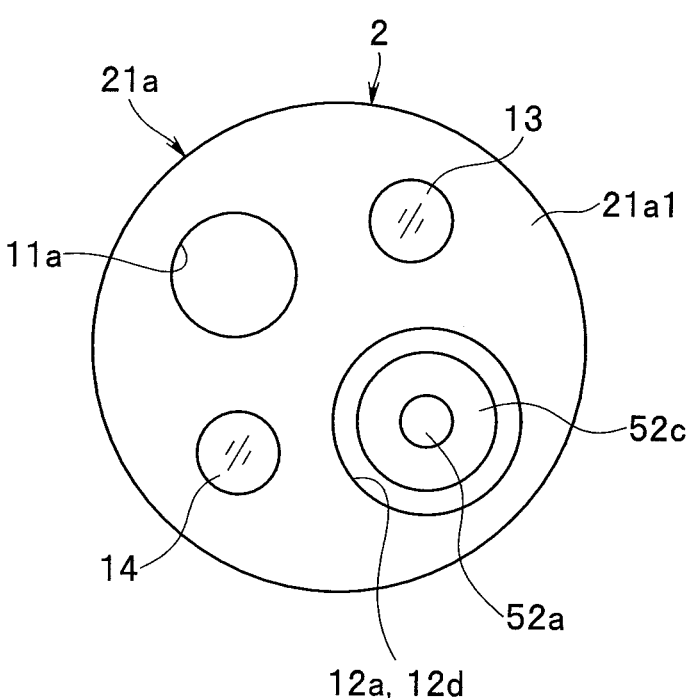
FIG. 13 is a front view showing a configuration of a distal end portion of an insertion portion of an endoscope in the above related embodiment.

FIG. 12 and FIG. 13 show an embodiment related to the present invention, and FIG. 12 is a cross-sectional view showing a structure of the suction channel 12 and the laser probe 52. FIG. 13 is a front view showing a configuration of the distal end portion 21a of the insertion portion 21 of the endoscope 2. In the related embodiment, portions similar to portions in the first and second embodiments are denoted by the same reference numerals, the description thereof will be appropriately omitted, and different points will be mainly described.

In the present embodiment, the small-diameter channel portion 12e is not provided in the suction channel 12 (accordingly, R2=R1); and the distal-end-side shaped portion 52c of the laser probe 52 is made larger in a diameter than the treatment instrument main body 52b, and is configured to satisfy R4>R3. In this case, the expression (1) is expressed as the following expression (3).

$$R1 - R3 \geq 2(R1 - R4) \tag{3}$$

The meaning of the expression (3) is the same as that described above in the expression (1), and the minimum value $(R1 - R3)/2$ of largest gaps between the suction channel 12 (inner diameter R1) and the probe main body 52b (outer diameter R3) is to become a largest diameter $(R1 - R4)$ of a calculus that can pass between the suction channel 12 and the distal-end-side shaped portion 52c (outer diameter R4).

According to such a related embodiment, effects similar to effects of the above described first and second embodiments can be achieved, and the clogging in the suction channel 12 can be reduced, even in a general endoscope in which the small-diameter channel portion 12e is not provided in the suction channel 12.

Note that the present invention is not limited to the above described embodiments as they are, and can be embodied by such modification of components as not to depart from the gist thereof, in an implementation stage. In addition, various aspects of the invention can be formed by appropriate combinations of a plurality of components that are disclosed in the above embodiments. For example, some components may be deleted from all the components shown in the embodiments. Furthermore, components in different embodiments may be appropriately combined. Thus, it goes without saying that various modifications and applications can be made without departing from the gist of the invention.

What is claimed is:

1. An endoscope, comprising:
an insertion portion configured to be inserted into a subject; and
a suction channel that comprises:
    a channel main body inserted in the insertion portion, and
    a small-diameter channel portion which is provided on a distal end side of the channel main body, includes a channel opening in a distal end face of the insertion portion, and has an inner diameter smaller than an inner diameter of the channel main body,
wherein the suction channel also serves as a treatment instrument channel,
wherein the suction channel is configured to suction, from the channel opening, a liquid along with a crushed calculus,
wherein the suction channel is configured to satisfy the following relational expression:

$$R1/R2 > 1.27,$$

where R1 represents an inner diameter of the channel main body and R2 represents an inner diameter of the small-diameter channel portion, and
    wherein the suction channel is configured to satisfy the following relational expression:

$$R1-R3 \geq 2(R2-R4),$$

with respect to a treatment instrument including a treatment instrument main body that is inserted into the channel main body and has an outer diameter R3, and a distal-end-side shaped portion that is inserted into the small-diameter channel portion and has an outer diameter R4.

2. The endoscope according to claim 1, wherein the suction channel is configured to further satisfy the following relational expression:

$$R1/R2 > 1.36.$$

3. The endoscope according to claim 1, wherein in the treatment instrument, the distal-end-side shaped portion has a larger diameter than the treatment instrument main body, and R4>R3 is satisfied.

4. The endoscope according to claim 3, wherein the treatment instrument can move in the suction channel in an axial direction of the insertion portion so that the treatment instrument main body is inserted into the small-diameter channel portion.

5. The endoscope according to claim 1, wherein:
in the treatment instrument, the distal-end-side shaped portion has a same outer diameter as an outer diameter of the treatment instrument main body, and R4=R3 is satisfied; and
the relational expression is expressed as:

$$R1-R3 \geq 2(R2-R3).$$

6. The endoscope according to claim 1, wherein the suction channel comprises a suction tube connector for connecting a suction tube that is connected to a suction pump.

7. An endoscope system, comprising:
an endoscope that comprises;
    an insertion portion configured to be inserted into a subject, and a suction channel that comprises:
        a channel main body inserted in the insertion portion, and
        a small-diameter channel portion which is provided on a distal end side of the channel main body, includes a channel opening in a distal end face of the insertion portion, and has an inner diameter smaller than an inner diameter of the channel main body,
    wherein the suction channel being is configured to suction, from the channel opening, a liquid along with a crushed calculus;
a calculus crushing device that comprises;
    a probe configured to protrude from the insertion portion and crush the calculus, and
    a generator configured to supply energy to the probe;
a pump configured to suction the liquid or cause the liquid to flow backward, along with the calculus through the suction channel; and
a treatment instrument comprising:
    a treatment instrument main body, which is inserted into the channel main body, and
    a distal-end-side shaped portion that is inserted into the small-diameter channel portion,
    wherein the suction channel is configured to satisfy the following relational expression:

$$R1/R2 > 1.27,$$

where R1 represents an inner diameter of the channel main body and R2 represents an inner diameter of the small-diameter channel portion,
    wherein the suction channel and the treatment instrument are configured to satisfy the following relational expression:

$$R1-R3 \geq 2(R2-R4),$$

where R3 represents an outer diameter of the treatment instrument main body and R4 represents an outer diameter of the distal-end-side shaped portion,
    wherein the suction channel also serves as a treatment instrument channel,
    wherein the treatment instrument is configured to be inserted in the suction channel, extend from the channel opening, and crush the calculus, and
    wherein the pump suctions the liquid along with the calculus from between the small-diameter channel portion and the distal-end-side shaped portion, through the channel opening.

8. The endoscope system according to claim 7, wherein the suction channel is configured to further satisfy the following relational expression:

$$R1/R2 > 1.36.$$

9. The endoscope system according to claim 7, wherein the treatment instrument includes a laser probe configured to crush the calculus by irradiation with laser.

10. The endoscope system according to claim 7, further comprising:
a liquid feeding channel that is inserted into the insertion portion and conveys a liquid,
wherein the pump suctions the liquid that is discharged from the liquid feeding channel into the subject and is perfused into the subject, along with the crushed calculus through the suction channel.

* * * * *